(12) United States Patent
Mah

(10) Patent No.: US 10,960,038 B2
(45) Date of Patent: Mar. 30, 2021

(54) OPTILUMINE COMPOSITION

(71) Applicant: DuraScience Inc., New York, NY (US)

(72) Inventor: James Nitit Mah, New York, NY (US)

(73) Assignee: Durascience, Inc., New York, NY (US)

( * ) Notice: Subject to any disclaimer, the term of this patent is extended or adjusted under 35 U.S.C. 154(b) by 33 days.

(21) Appl. No.: 16/679,284

(22) Filed: Nov. 10, 2019

(65) Prior Publication Data

US 2020/0069756 A1 Mar. 5, 2020

(51) Int. Cl.
*A61K 36/28* (2006.01)
*A61K 36/54* (2006.01)
*A61K 31/05* (2006.01)

(52) U.S. Cl.
CPC .............. *A61K 36/28* (2013.01); *A61K 31/05* (2013.01); *A61K 36/54* (2013.01)

(58) Field of Classification Search
CPC ....................................................... A61K 36/00
USPC ........................................................ 424/725
See application file for complete search history.

(56) References Cited

U.S. PATENT DOCUMENTS

2008/0305132 A1* 12/2008 Karol .................. A61K 8/9794
424/401

* cited by examiner

*Primary Examiner* — Michael V Meller

(57) ABSTRACT

In an embodiment, a nutritional supplement composition is provided. The nutritional supplement composition is provided including a combination of 100 mg of avocado oil, 15 mg of zeaxanthin of a five percent concentration and 20 mg marigold extract from the tagetes erecta strain. The nutritional supplement is in the form of a compound known as OPTILUMINE™.

2 Claims, No Drawings

OPTILUMINE COMPOSITION

BACKGROUND

In the past, we commonly used all parts of natural foods when we consumed a meal. Human eating patterns naturally accessed nutrients available from what was eaten and very little nutrients were wasted as a result. For example, when eating fish, the muscular parts of the fish were consumed along with other parts such as connective tissue. When eating plants, the edible portion of the plant was consumed in its entirety. Our bodies would then filter out what was not consumable, such as the outer shell of a kernel of corn for example. As this occurred, our bodies would extract what nutrients could be found in the food to sustain and grow the human form. This allowed use of local foods to provide nutrients which were available, but was somewhat limited in that foods not available locally could not be used in most cases. Over time, we learned to travel and to ship food from where it was produced to where it could be consumed. Additionally, we learned to prepare foods, removing portions of the food which were either inedible, or undesirable. Removing the inedible parts typically provided some benefit, while parts that were simply undesirable sometimes held valuable ingredients.

Avocado oil is an edible oil pressed from the fruit of the Persea americana (avocado). Avocados are found in various parts of the world, including Mexico, the United States (principally California and Florida), the Dominican Republic, Colombia, Peru and Indonesia.

Zeaxanthin is one of the most common carotenoid alcohols found in nature. It is important in the xanthophyll cycle. Synthesized in plants and some micro-organisms, it is the pigment that gives paprika (made from bell peppers), corn, saffron, wolfberries, and many other plants and microbes their characteristic color.

Tagetes erecta, the Mexican marigold or Aztec marigold, is a species of the genus Tagetes native to Mexico. Despite its being native to the Americas, it is often called African marigold.

SUMMARY OF THE INVENTION

A nutritional supplement composition is provided including a marigold extract from the tagetes erecta strain, avocado oil and zeaxanthin of a five percent concentration. The nutritional supplement is in the form of a compound known as OPTILUMINE™.

The foregoing, and other features and advantages of various embodiments of the invention, will be apparent from the following, more particular description of the embodiments of the invention, any accompanying drawings, and the claims.

DETAILED DESCRIPTION

A composition is provided as OPTILUMINE™. The specific embodiments described in this document represent exemplary instances of the present invention, and are illustrative in nature rather than restrictive.

In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments.

Avocado oil is a relatively good source of lutein, a carotenoid naturally found in human eyes. It functions as an antioxidant that has benefits for eye health. Lutein may reduce the risk of cataracts and macular degeneration, which are common age-related eye diseases. The human body does not produce lutein, so you must obtain it from your diet.

Avocado oil is rich in oleic acid. Almost 70% of avocado oil consists of heart-healthy oleic acid, a monounsaturated omega-9 fatty acid.

Studies also indicate avocado oil Reduces Cholesterol and Improves Heart Health Additionally, fats from avocado oil enhance absorption of other nutrients in the body.

Studies have also found that avocado oil reduces the symptoms of arthritis, such as painful inflammation of joints. Similarly, avocado oil has been associated with the effect of reducing periodontal (gum) disease. Avocado oil has also been found to improve skin and promote wound healing. Also, avocado oil appears to neutralize some free radicals, reducing damage associated with such free radicals.

Several observational studies have provided preliminary evidence for high dietary intake of foods including lutein and zeaxanthin with lower incidence of age-related macular degeneration, most notably the Age-Related Eye Disease Study Zeaxanthin can help protect human eyes from harmful high-energy light waves such as ultraviolet rays in sunlight. Also, studies suggest that a high level of both zeaxanthin and lutein in eye tissue is linked with better vision, especially in dim light or where glare is a problem.

Diets rich in these two nutrients may also help hold off age-related eye diseases. One study found that people who ate foods rich in zeaxanthin may be half as likely to get cataracts. Another study showed that for sufferers of macular degeneration, which causes damage to the middle of the retina and can take away central vision capabilities, using supplements with lutein and zeaxanthin can slow its progress.

Since time immemorial, tagetes erecta (Marigold) has been used for medicinal purposes. Native Americans used it as a skin wash and for yellow dye. The pigments of the tagetes erecta are colored due to the presence of carotenoids, of which the main one is lutein, which is associated with the prevention of the development of age-related eye diseases such as cataracts and macular degeneration. In some regions of Mexico it is used in digestive ailments, such as stomach pain, as well as diarrhea, colic, liver problems, bile, vomiting, and indigestion. The plant also produces intestinal washes, and is used against intestinal parasites and as a carminative. The most intense orange tones of the flowers involve a higher content of carotenoids, especially xanthophyll. Some studies indicate the effectiveness of xanthophyll in prevention of coronary artery disease, heart attacks, immune response, old age and cancer. Other uses include respiratory diseases such as colds, flu, bronchitis and nasal congestion as well as gynecological problems.

The benefit of the composition includes restoring and enhancing cells. Our cells constantly deteriorate in daily life. If there is no support to restore the deterioration, cellular damage will affect the body functions. OPTILUMINE™ composition is a supplementary factor that can restore the cells to the body balance without drug and substance usage. When cells are restored, in the next process, OPTILUMINE™ composition may accordingly boost cell strength, equivalent to increasing the effectiveness and the number of cells, while maximizing physical and mental abilities After the cellular restoration and boosting the cell strength, the next challenge is the protection to maintain the long-lasting quality of the cells. OPTILUMINE™ dietary supplement may help to protect and delay the cellular deterioration. This will also result in improving the immune system, as the immune system no longer needs to activate against inflammation or other forms of deterioration. When the cell functions are systematically restored, boosted and protected, OPTILUMINE™ dietary supplement may directly enhance physical and mental capacity to go beyond limits at each age and to live life fully as the pace of life requires a strong response to maintain youth and vigor.

The health benefits of OPTILUMINE™ are also potentially of value to children, and help to develop the strength of new cells and protect cells from early deterioration. Both are beneficial to the development of body, intelligence, memory, and positive emotions. The physical results may include i) restore cells for normal growth in each stage, ii) recover from illness, iii) build muscle, v) boost the immune system, vi) reduce the risk of the incidence of disease, vii) promote growth to maximum effectiveness, viii) adjust height, ix) improve body growth, x) efficient immunity and xi) increase energy. The wound and injury healing properties are potentially of particular assistance to children, as the nutrients provided assist specifically with structures often injured in sports or other childhood activities.

The composition also helps to restore the old damaged cells, repair damaged body tissues, delay the cellular deterioration, inhibit free radicals, and help the process of skin cell renewal in adults for glowing skin and younger appearance. Providing building blocks as previously mentioned contribute to enhancing balance, reducing exhaustion from stress and demands of healing, improving concentration and work efficiency, reducing healing time and longer term pain, and boosting the immune system to stay healthy Physical results may also include: a radiant and vibrant skin, younger appearance; reducing fatigue at work; restoring the reproductive system; refreshing the body; boosting the immune system; protecting against free radical formation; and preventing premature aging.

The compounds are typically dried and ground or milled to small particles, and subsequently combined in the desired ratio. The combination may remain as a powder to be added to food or pressed in a tablet. Alternatively, the compounds may be mixed in an aqueous or other liquid solution and thereby provided in liquid form.

In an embodiment, a preferred dosage, the total compound blended is 135 mg, pressed into a single tablet. The compound may be sold under the OPTILUMINE™ name. The dosage may include a combination of 100 mg of avocado oil, 15 mg of zeaxanthin of a five percent concentration and 20 mg marigold extract from the tagetes erecta strain. However, other ratios of the ingredients may be provided, and smaller or larger dosages may be used for particular applications.

Study of OPTILUMINE™ Effectiveness

A study of users of a trial formulation was conducted. The study focused primarily on ocular considerations, but also considered other possible results. Participants reported the following results:

Eighty-two percent (82%) of participants reported decreased incidence of mature cataracts, with a response of up to seventy percent (70%) decrease in incidence of such cataracts as a measured result.

Ninety-four percent (94%) of participants reported reduced evidence of macular degeneration, with a measured result of sixty percent (60%) reduced risk compared to typical results for similar individuals.

Ninety percent (90%) of participants reported better results on visual acuity tests. The participants reported a measured result of fifty percent (50%) better performance on such visual acuity tests.

Ninety-four percent (94%) of participants reported decreased night-time glare effects. The participants reported up to an eighty percent (80%) decrease in glare duration in such situations.

Ninety-six percent (96%) of participants also reported increases in contrast sensitivity. Measured as an ability to distinguish an object from a background, participants saw a typical seventy percent (70%) increase in results of such a test.

Ninety-two percent (92%) of participants reported decreased eye sensitivity to eye strain, with a typical measured result of an eighty percent (80%) increase in duration of screen reading time as a result.

Ninety-six percent (96%) of participants reported a decrease in dryness of eyes or corresponding increase in eye lubrication, showing as much as eighty percent (80%) less eye dryness.

Eighty-six percent (86%) of participants reported better resistance to eye infections. The participants reported an eighty percent (80%) decrease in incidence of eye infections.

Eighty-two percent (82%) of participants reported improved intra-ocular pressure, typically reporting an eighty percent (80%) decrease in incidence of glaucoma symptoms.

One skilled in the art will appreciate that although specific examples and embodiments of the system and methods have been described for purposes of illustration, various modifications can be made without deviating from present invention. For example, embodiments of the present invention may be applied to many different types of databases, systems and application programs. Moreover, features of one embodiment may be incorporated into other embodiments, even where those features are not described together in a single embodiment within the present document.

What is claimed is:

1. A tablet consisting essentially of a marigold extract, avocado oil, and zeaxanthin.

2. The tablet of claim 1, wherein the marigold extract is in an amount of 20 mg, the avocado extract is in an amount of 100 mg and the zeaxanthin is in an amount of 40 mg.

* * * * *